CHRYSANTHEMUM PLANT
Filed July 21, 1975
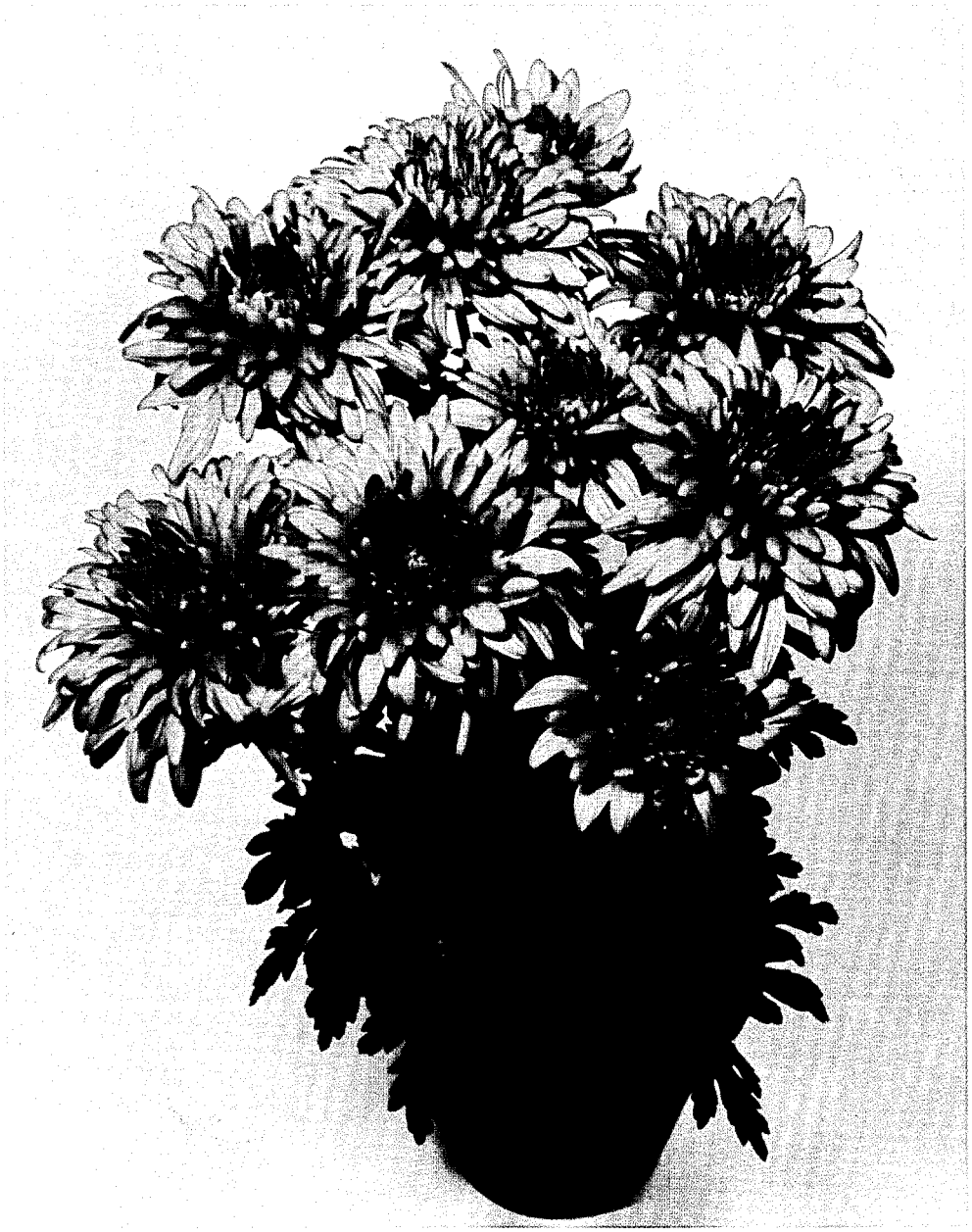

United States Patent

Plant Pat. 3,955
Patented Oct. 12, 1976

3,955

CHRYSANTHEMUM PLANT

John Robert Culbert, Monticello, Ill., assignor to University of Illinois Foundation, Urbana, Ill.

Filed July 21, 1975, Ser. No. 597,407
Int. Cl.[2] A01H 5/00
U.S. Cl. Plt.—81 1 Claim The present invention relates to a new and distinct cultivar of chrysanthemum plant asexually reproduced by cuttings from a sport that occurred naturally on one of four shoots of a chrysanthemum plant among those plants grown by the Department of Horticulture, University of Illinois, Urban, Ill., which are the subject of U.S. Plant Pat. No. 3,408.

Successive propagations of my new cultivar have retained the distinctive unique characteristics thereof, to wit:

1. Strong reddish purple decorative flowers 4½" to 5" in diameter when produced on a pinched plant and disbudded to 1 flower per stem;
2. Flower color decidedly resistant to fading even when grown and flowered under extremely high temperatures and full intensity of the sun;
3. Flowering response of approximately 9 weeks from start of initiation and decidedly resistant to delay or "stall" induced by extremely high temperatures;
4. Slow opening of the ray florets and ability to retain its form result in long "shelf life" or keeping quality; and,
5. Strong plants that average 4 to 5 breaks per pinched plant.

My new cultivar, when grown in the vicinity of Urbana, Ill., has a response period of approximately 9 weeks from start of initiation, and the following detailed description is based on observations made of the new cultivar in the Floriculture greenhouses in Urbana, Ill. The response time, blooming period, color, and total vigor may vary significantly with varying environmental conditions such as temperature, day length, light intensity and amount of carbon dioxide in the greenhouse atmosphere.

The following chart outlines the variation of flowering response pattern experienced for the various seasons in Urbana, Ill. with carbon dioxide injected into the greenhouse when possible.

| Months: | Flowering response pattern at Urbana, Ill. |
|---|---|
| March through May | Mid 8 week. |
| June and July | 9 week. |
| August and September | Late 9 week. |
| October and November | Early 9 week. |
| December through February | 9 week. |

Suggested period for flowering with superior results in the north central United States is from April through November. Satisfactory results may be obtained in the above area from December through March.

The accompanying drawing shows the unique characteristics of my new cultivar, the color being as nearly true as possible with color illustrations of this type. Color references are made to the Nickerson Color Fan published by Munsell Color Co., 1957.

Botanical classification: *Chrysanthemum morifolium* Ramat.

BLOOM

Size (when disbudded and fully expanded): 4½" to 5".
Depth (when disbudded and fully expanded): 1½" to 2".

Form: Decorative type, almost or fully double; inner ray florets remain erect as outer florets assume first a horizontal and later a slightly reflexed position; inner florets later flatten.
Borne: Clusters on elongated pedicels.
Stems: Strong.
Permanence: 14 to 18 days.
Petals (ray florets):
- *Color.*—Center of flower—Strong reddish purple, 2.5RP 4/10. Tips of florets—Strong reddish purple, 2.5 RP 5/10. Base of florets—Brilliant yellow green, 2.5 GY 9/8. Reverse of florets—Moderate purplish pink, 2.5 RP 7/8. Overall tonality—Strong reddish purple, 2.5 RP 5/10. Discoloration—None.
- *Form.*—Linear with apex obtuse; flat.
- *Number.*—330 to 380.
- *Arrangement.*—Composite, whorled in a single receptacle.
- *Texture.*—Smooth.
- *Fragrance.*—Typical chrysanthemum.
- *Persistence.*—Strongly resist shattering.

*Disc florets*
- *Color.*—Brilliant greenish yellow 7.5Y 9/8.
- *Form.*—Tubular.
- *Size.*—Length ¼"; diameter 1/16".
- *Number.*—None to 5.

*Reproductive organs*:
- *Stamens, anthers.*—Epipetalous and syngenesious in disc florets. Number.—None to 25. Arrangement.—Clustered in center of bloom, if present. Pollen.—None to very sparse. Color.—Vivid yellow, 2.5Y 8/12.
- *Pistol.*—Style: Number.—1 per each ray or disc floret. Length.—Short. Stigma: Number.—2 per each style. Ovary: Position.—At base of ray or disc floret attached to receptacle.

PLANT

Form: Herbaceous perennial.
Growth: Spreading.
Height: Average height 12" (range 9" to 15") when pinched and given 9 week medium treatment during the various seasons of the year.
Spread: Average spread 17" (range 15" to 19") when pinched and given 9 week medium treatment during the various seasons of the year.
Foliage:
- *Color.*—Top side.—Moderate olive green, 7.5 GY 4/4. Bottom side.—Moderate yellow green, 7.5 GY 5/7.
- *Size.*—Average length 3"; average width 1¾" (range: length 2" to 4½"; width 1½" to 2½").
- *Quantity.*—12 to 16 leaves per 6" stem when pinched and given 9 week medium treatment during the various seasons of the year.
- *Shape.*—Simple, obovate.
- *Margin.*—Deeply lobed.
- *Base.*—Hastate.
- *Apex.*—Acute.
- *Venation.*—Pinnate, prominent.
- *Texture.*—Coarse.
- *Stipules.*—Rudimentary.

What is claimed is:

1. A new and distinct cultivar of chrysanthemum plant substantially as herein shown and described, characterized particularly as to novelty by decorative type flowers of strong reddish purple color that resist fading to a remarkable degree even when exposed to extremely high temperatures and which open slowly and retain their form over a long time extending the useful "shelf life," by flower buds which develop normally in approximately 9 weeks from start of initiation without delay or stall even when grown under extremely high temperatures, and by strong plants which average 4 to 5 breaks per pinched plant making a showy display of the 4½" to 5" flowers.

No reference cited.

ROBERT E. BAGWILL, Primary Examiner